United States Patent
Hankey et al.

(10) Patent No.: US 11,410,523 B2
(45) Date of Patent: Aug. 9, 2022

(54) CARE EVENT DETECTION AND ALERTS

(71) Applicant: Apple Inc., Cupertino, CA (US)

(72) Inventors: Martha E. Hankey, San Francisco, CA (US); James Foster, Oxford (GB)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 16/804,410

(22) Filed: Feb. 28, 2020

(65) Prior Publication Data

US 2020/0202696 A1 Jun. 25, 2020

Related U.S. Application Data

(63) Continuation of application No. 14/849,427, filed on Sep. 9, 2015, now Pat. No. 10,593,186.

(60) Provisional application No. 62/047,781, filed on Sep. 9, 2014.

(51) Int. Cl.
| | |
|---|---|
| *G08B 21/04* | (2006.01) |
| *A61B 5/0205* | (2006.01) |
| *G08B 21/02* | (2006.01) |
| *G08B 25/00* | (2006.01) |
| *G08B 25/01* | (2006.01) |

(52) U.S. Cl.
CPC ........ *G08B 21/0453* (2013.01); *A61B 5/0205* (2013.01); *G08B 21/0211* (2013.01); *G08B 21/043* (2013.01); *G08B 21/0446* (2013.01); *G08B 25/005* (2013.01); *G08B 25/016* (2013.01)

(58) Field of Classification Search
CPC ............ G08B 21/0453; G08B 21/0446; G08B 21/0211; G08B 21/02; G08B 25/005; G08B 25/001; G08B 21/043; G08B 25/016; A61B 5/0205

See application file for complete search history.

(56) References Cited

U.S. PATENT DOCUMENTS

| | | | |
|---|---|---|---|
| 5,348,008 A | 9/1994 | Bomn et al. | |
| 6,081,742 A * | 6/2000 | Amano | A61B 5/0205 600/484 |
| 6,364,834 B1 | 4/2002 | Reuss et al. | |
| 8,680,989 B2 | 3/2014 | George | |
| 8,952,818 B1 * | 2/2015 | Zhang | G08B 21/043 701/300 |
| 9,028,407 B1 * | 5/2015 | Bennett-Guerrero | A61B 5/4809 340/573.1 |
| 9,554,706 B2 | 1/2017 | Soomro et al. | |

(Continued)

*Primary Examiner* — Hongmin Fan
(74) *Attorney, Agent, or Firm* — Treyz Law Group, P.C.; David K. Cole

(57) ABSTRACT

An occurrence of one or more "care events" is detected by an electronic device monitoring environmental data and/or user data from one or more sensors. The electronic device transmits one or more alerts regarding the detected occurrence to at least one other electronic device. In some cases, the electronic device may cooperate with at least one other electronic device in monitoring, detecting, and/or transmitting. For example, the electronic device may detect the occurrence based on sensor data received from a cooperative electronic device or such data in combination with the electronic device's sensor data. By way of another example, the electronic device may detect the occurrence and signal a cooperative electronic device to transmit one or more alerts.

18 Claims, 8 Drawing Sheets

(56) References Cited

U.S. PATENT DOCUMENTS

| | | | |
|---|---|---|---|
| 2003/0058111 A1* | 3/2003 | Lee | G08B 13/19641 348/E7.086 |
| 2005/0151640 A1 | 7/2005 | Hastings | |
| 2005/0151642 A1* | 7/2005 | Tupler | H04W 76/50 340/539.18 |
| 2006/0145874 A1* | 7/2006 | Fredriksson | G08B 21/0446 340/573.1 |
| 2008/0133277 A1 | 6/2008 | Jang et al. | |
| 2008/0303660 A1 | 12/2008 | Lombardi | |
| 2009/0165022 A1 | 6/2009 | Madsen et al. | |
| 2009/0322548 A1* | 12/2009 | Gottlieb | G08B 21/0446 340/686.6 |
| 2010/0297981 A1 | 11/2010 | Ballantyne et al. | |
| 2010/0331713 A1 | 12/2010 | Ostrow | |
| 2011/0245633 A1 | 10/2011 | Goldberg et al. | |
| 2011/0288379 A1 | 11/2011 | Wu | |
| 2012/0046606 A1 | 2/2012 | Arefieg | |
| 2012/0078071 A1 | 3/2012 | Bohm et al. | |
| 2012/0293323 A1 | 11/2012 | Kaib et al. | |
| 2013/0082842 A1* | 4/2013 | Balazs | G08B 21/043 340/573.1 |
| 2013/0122849 A1* | 5/2013 | Doezema | H04W 4/90 455/404.1 |
| 2013/0231574 A1* | 9/2013 | Tran | A61B 5/0537 600/479 |
| 2013/0297350 A1 | 11/2013 | Gross et al. | |
| 2013/0331058 A1 | 12/2013 | Harvey | |
| 2014/0087685 A1 | 3/2014 | Kellond et al. | |
| 2014/0135588 A1 | 5/2014 | Al-Ali et al. | |
| 2014/0206293 A1 | 7/2014 | Sanchez-Valenzuela et al. | |
| 2014/0206948 A1 | 7/2014 | Romem | |
| 2014/0266690 A1 | 9/2014 | McKinley et al. | |
| 2014/0276238 A1* | 9/2014 | Osorio | G08B 21/0446 600/595 |
| 2014/0288435 A1 | 9/2014 | Richards et al. | |
| 2015/0179050 A1 | 6/2015 | Katingari et al. | |
| 2015/0244855 A1 | 8/2015 | Serra et al. | |

* cited by examiner

CARE EVENT DETECTION AND ALERTS

CROSS-REFERENCE TO RELATED APPLICATION(S)

This application is a continuation of U.S. patent application Ser. No. 14/849,427, filed Sep. 9, 2015, which claims the benefit of provisional patent application No. 62/047,781, filed Sep. 9, 2014, both of which are hereby incorporated by reference herein in their entireties.

FIELD

This disclosure relates generally to care events, and more specifically to detection of care events and transmission of alerts regarding detected care events.

BACKGROUND

Care events may be any event that may occur for which a user may need care. For example, care events may include a car crash, a bike accident, a medical emergency such as a heart attack or an aneurysm, separation of a child from the child's caregiver, a dementia patient becoming lost, an avalanche, a fall, a mugging, a fire, and/or any other event for which a user may require medical, police, family, fire rescue, and/or other kind of assistance.

In order for the user to receive care for such a care event, one or more individuals or entities who provide such care (such as friends, family, firefighters, ambulances, hospitals, police, and so on) may need to be alerted to the fact that the care event has occurred. Often, the user may contact such individuals or entities upon the occurrence of the event. For example, a user who has been in a car crash may telephone emergency services for an ambulance. However, in many cases the user may be incapacitated and/or otherwise unable to initiate communications regarding the care event.

SUMMARY

The present disclosure discloses systems, methods, and apparatuses for providing alerts regarding a care event. An occurrence of one or more "care events" may be detected by an electronic device monitoring environmental data and/or user data from one or more sensors. The electronic device may transmit one or more alerts regarding the detected occurrence to at least one other electronic device. In some cases, the electronic device may cooperate with at least one other electronic device in monitoring, detecting, and/or transmitting. For example, the electronic device may detect the occurrence based on sensor data received from a cooperative electronic device or such data in combination with the electronic device's sensor data. By way of another example, the electronic device may detect the occurrence and signal a cooperative electronic device to transmit one or more alerts.

In some implementations, detection of whether or not a care event has occurred may be dependent upon a context of the electronic device, such as a detected location or speed of travel of the electronic device.

In various implementations, the alerts may be transmitted to electronic devices listed in a care list, which may be user defined. Such a care list may be a data record indicating parties whom should be alerted in case of an occurrence and how they should be alerted. In some cases, a care list may have multiple levels where an alert for an occurrence is transmitted to a first set of list members and then to a second set of list members if an escalation condition occurs. Further, such a care list may also include conditions specifying different procedures to be followed in transmitting alerts based on factors such as the particular occurrence detected, a context of the electronic device, and so on.

In some implementations, information associated with the occurrence may be included in the transmitted alert. In various cases, the electronic device may present one or more prompts upon detection of an occurrence and alerts may be transmitted if a user does not enter input indicating not to transmit alerts within a timeout period. In such cases, information such as a failure to respond to such a prompt, an indication of an affirmative response to such a prompt, an affirmative response, and so on may also be included in the transmitted alert.

In various implementations, the electronic device may present one or more notifications regarding the detection of the occurrence. For example, the electronic device may display and/or otherwise medical information for a user when an occurrence is detected and may provide one or more haptic outputs to indicate that the medical information is being provided. In addition and/or in the alternative to the electronic device providing such notifications, the electronic device may signal other proximate electronic devices to provide such notifications. In various cases, the electronic device may switch into one or more power saving modes when an occurrence is detected in order to preserve power for presenting notifications, transmitting alerts, and so on.

In some implementations, environmental data may relate to connection of the electronic device to a monitored device and/or the relationship of the electronic device to a geographical boundary. As such, an occurrence may be detected when a signal is not received from the monitored electronic device within a period of time, the monitored electronic device moves more than a threshold distance from the electronic device, the electronic device crosses the geographical boundary, and so on.

In various embodiments, a system for providing alerts regarding a care event includes an electronic device having at least one non transitory storage medium that stores instructions and at least one processing unit that executes the instructions to: detect occurrence of at least one care event by monitoring at least one of environment data or user data from at least one sensor and transmit at least one alert regarding the detected occurrence to at least one other electronic device.

In some embodiments, an electronic device includes at least one non transitory storage medium that stores instructions and at least one processing unit that executes the instructions to: detect occurrence of at least one care event by monitoring at least one of environment data or user data from at least one sensor and transmit at least one alert regarding the detected occurrence to at least one other electronic device.

In one or more embodiments, a method for providing alerts regarding a care event includes detecting occurrence of at least one care event utilizing an electronic device by monitoring at least one of environment data or user data from at least one sensor and transmitting at least one alert regarding the detected occurrence to at least one other electronic device.

It is to be understood that both the foregoing general description and the following detailed description are for purposes of example and explanation and do not necessarily limit the present disclosure. The accompanying drawings, which are incorporated in and constitute a part of the specification, illustrate subject matter of the disclosure.

DETAILED DESCRIPTION

Figure 1:
FIG. 1 is a diagram illustrating a system for providing alerts regarding a care event.

The description that follows includes sample systems, methods, and computer program products that embody various elements of the present disclosure. However, it should be understood that the described disclosure may be practiced in a variety of forms in addition to those described herein.

The present disclosure discloses systems, methods, and apparatuses for providing alerts regarding a care event. An occurrence of one or more "care events" (any event for which a user may need care) may be detected by an electronic device monitoring environmental data (data regarding the environment around the electronic device and/or surrounding area) and/or user data (data regarding a user of the electronic device and/or related users) from one or more sensors. The electronic device may transmit one or more alerts regarding the detected occurrence to at least one other electronic device. In some cases, the electronic device may cooperate with at least one other electronic device (a cooperative electronic device) in monitoring, detecting, and/or transmitting. For example, the electronic device may detect the occurrence based on sensor data received from a cooperative electronic device or such data in combination with the electronic device's sensor data. By way of another example, the electronic device may detect the occurrence and signal a cooperative electronic device to transmit one or more alerts.

In various implementations, the alerts may be transmitted (singly, periodically, and/or otherwise transmitted) to electronic devices listed in a care list, which may be user defined. Such a care list may be a data record indicating parties whom should be alerted in case of an occurrence and how they should be alerted (i.e., contact information and/or what communication medium to utilize). In some cases, a care list may have multiple levels where an alert for an occurrence is transmitted to a first set of list members (such as family members) and then to a second set of list members (such as emergency services) if an escalation condition occurs (such as elapse of a time period from transmission of the alert to the first set of list members). Further, such a care list may also include conditions specifying different procedures to be followed in transmitting alerts based on factors such as the particular occurrence detected (such as transmitting alerts to multiple levels of members without an escalation condition for more severe occurrences), a context of the electronic device (such as transmitting alerts to emergency services instead of family when the electronic device is located outside the user's home country or using an alternative communication medium address instead of a preferred communication medium address when the electronic device is unable to utilize the preferred communication medium), and so on.

In some implementations, information associated with the occurrence (such as the environmental data, the user data, a portion of the environmental data or user data, information regarding the user or electronic device, medical records and/or other medical data for the user, position information, and so on) may be included in the transmitted alert. In various cases, the electronic device may present one or more prompts (audio, visual, and so on) upon detection of an occurrence and alerts may be transmitted if a user does not enter input (whether by touch input, button or key press, voice response, motion response such as a head shake captured by camera) indicating not to transmit alerts within a timeout period. In such cases, information such as a failure to respond to such a prompt, an indication of an affirmative response to such a prompt, an affirmative response, and so on may also be included in the transmitted alert.

In various implementations, detection of whether or not a care event has occurred may be dependent upon a context of the electronic device, such as a detected location or speed of travel of the electronic device. For example, a user's heart rate may be monitored to determine whether or not a user has a cardiac problem. However, a heart rate for a care event should be detected may be different when a user is exercising as opposed to when the user is not exercising. As such, an occurrence may not be detected for a higher heart rate when a location of the electronic device is detected as the user's gym or when the electronic device is travelling at a speed indicating that the user is jogging unless the heart rate is within a range that is excessive for exercise as well.

In some implementations, the electronic device may present one or more notifications regarding the detection of the occurrence. For example, the electronic device may display and/or otherwise medical information for a user (such as medical conditions, allergies, medical history, physician information, identification information, and so on) (and/or information regarding the occurrence that was detected) when an occurrence is detected and may provide one or more haptic outputs to indicate that the medical information is being provided. In addition and/or in the alternative to the electronic device providing such notifications, the electronic device may signal other proximate electronic devices (such as via Bluetooth or other communication media) to provide such notifications. In various cases, the electronic device may switch into one or more power saving modes (such as multiple modes that use progressively less power that are progressively switched to upon the elapse of successive time periods from the detection of an occurrence) when an occurrence is detected in order to preserve power for presenting notifications, transmitting alerts, and so on.

In various implementations, environmental data may relate to connection of the electronic device to a monitored device and/or the relationship of the electronic device to a geographical boundary. As such, an occurrence may be detected when a signal is not received from the monitored electronic device within a period of time, the monitored electronic device moves more than a threshold distance from the electronic device, the electronic device crosses the geographical boundary, and so on.

The electronic device may monitor environmental data and/or user data from a variety of different sensors of the electronic device and/or one or more cooperative electronic devices to determine whether or not a care event has occurred. Such sensors may include, but are not limited to one or more accelerometers, gyroscopes, cameras, altimeters, microphones, motion sensors, photoplethysmogram (PPG) sensors, galvanic skin detectors, global positioning system (GPS) devices, communication components, heart rate monitors, respiratory system monitors, blood pressure monitors, temperature sensors, and/or any other kind of sensor. In some cases, the electronic device may present one or more notifications regarding data from monitored sensors prior to the detection of an occurrence, such as where the monitored data indicates that an event may soon occur (such as where a combination of accelerometer data and GPS data indicates that a user is in a speeding car and may soon be in an accident).

FIG. 1 is a diagram illustrating a system 100 for providing alerts regarding a care event. The system may include an electronic device 101 that monitors environmental data and/or user 102 data to detect the occurrence of one or more care events and transmit one or more alerts regarding the detected occurrence to one or more other electronic devices.

As illustrated, the electronic device 101 is a fitness monitor worn on the bicep of a user 102. However, it is understood that this is an example. In various implementations, the electronic device may be any kind of electronic device such as a mobile computer, a tablet computer, a laptop computer, a desktop computer, a cellular telephone, a wearable device, a heart rate monitor, a respiratory monitor, a smart phone, a digital media player, and/or any other kind of electronic device.

In some implementations, the electronic device 101 may cooperate with one or more electronic devices 103 in detecting the occurrence, transmitting the alerts, and/or performing other functions. As illustrated, the cooperative electronic device 103 is a smart phone in a shirt pocket 104 of the user 102. However, it is understood that this is an example and that in various cases any kind or number of electronic devices (such as the examples provided for the electronic device above) may cooperate with the electronic device.

Figure 2:
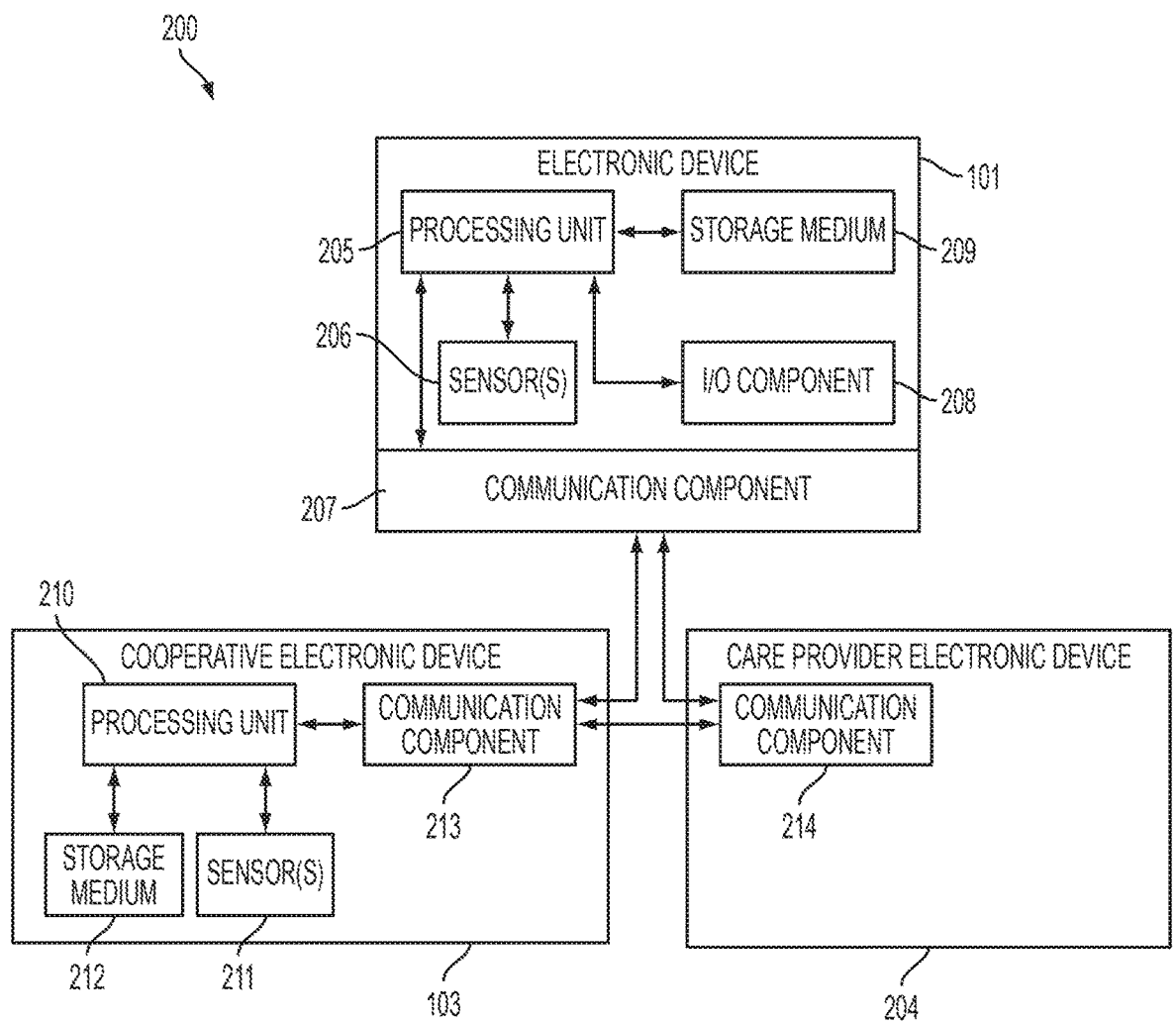
FIG. 2 is a block diagram illustrating relationships between functional components of a system for providing alerts regarding a care event.

FIG. 2 is a block diagram illustrating relationships between functional components of a system for providing alerts regarding a care event. The system 200 may include an electronic device 101, one or more cooperative electronic devices 103 (referenced as such because it is a device with which the electronic device is configured to cooperate), and/or one or more care provider electronic devices 204 (referenced as such because it is a device for which the electronic device is configured to transmit alerts to regarding care events).

As illustrated, the electronic device 101 may include one or more processing units 205, one or more sensors 206 (such as one or more accelerometers, gyroscopes, cameras, altimeters, microphones, motion sensors, PPG sensors, galvanic skin detectors, GPS devices, communication components, heart rate monitors, respiratory system monitors, blood pressure monitors, temperature sensors, and/or any other kind of sensor), one or more communication components 207 (which may be any kind of wired and/or wireless communication components such as a cellular antenna, a Bluetooth or Bluetooth low energy antenna, a near field communication antenna, a WiFi antenna, an infra-red transmitter and/or receiver, an Ethernet adapter, and/or other such communication component), one or more input/output components 208 (such as one or more displays, speakers, microphones, touch screens, mice, keyboards, virtual keyboards, touch pads, track pads, and so on), and/or one or more non-transitory storage media 209 (which may take the form of, but is not limited to, a magnetic storage medium; optical storage medium; magneto-optical storage medium; read only memory; random access memory; erasable programmable memory; flash memory; and so on).

Similarly, a cooperative electronic device 103 may include one or more processing units 210, sensor(s) 211, storage media 212, communication components 213, and/or other components. Likewise, a care provider electronic device 204 may include one or more communication components 214 and/or various other components such as those listed above for the electronic device 101.

As described above the electronic device 101 may cooperate with one or more cooperative electronic devices 103 to detect the occurrence of a care event, transmit alerts regarding a detected care event, and/or perform other functions.

For example, in some cases the cooperative electronic device 103 may include one or more sensors 211 that detect environmental data and/or user data and the electronic device 101 may not include such sensors. Instead, the electronic device may receive and monitor data from such sensors via the communication components 207 and 213. The electronic device may determine from the monitored received data that a care event has occurred. The electronic device may transmit one or more alerts regarding such a detected care event to one or more care provider electronic devices 204 via the communication components 207 and 214.

By way of another example, the cooperative electronic device 103 may monitor data from sensors 211 and transmit one or more indications to the electronic device 101 when a care event occurs. As such, the electronic device may determine that a care event has occurred when such an indication is received and may transmit one or more alerts regarding such a detected care event to one or more care provider electronic devices 204.

By way of still another example, the electronic device 101 may monitor data from both sensor(s) 206 and received data from sensor(s) 211 to determine that a care event has occurred. In an example case, a sensor 206 may monitor a user's heart rate while a sensor 211 monitors acceleration. The electronic device may determine from the sensor 206 that a heart rate is no longer detected and from the sensor 211 that a sudden acceleration before a stop was detected. From these two pieces of data, the electronic device may determine that the user has had a heart attack and fallen to the ground incapacitated. As such, the electronic device may transmit one or more alerts.

In another example, the electronic device 101 may determine whether or not a care event has occurred utilizing data from the sensor(s) 206, but may obtain other information for transmitting the alert from the cooperative device 103. In one example case, the cooperative electronic device may include a GPS device but the electronic device may not. As such, the electronic device may obtain GPS information from the cooperative electronic device when a care event is detected so that the electronic device may include the GPS in transmitted alerts.

In another example case, the cooperative electronic device 103 may include a communication component 211 that can access medical information (such as medical records) for the user (such as a cellular antenna, a WiFi antenna, and so on) whereas the electronic device may only include a communication component 207 that can communicate with the cooperative electronic device. As such, the electronic device may obtain medical information from the cooperative electronic device when a care event is detected so that the electronic device may include the medical in transmitted alerts. Alternatively, the electronic device may signal the cooperative electronic device to separately transmit such medical information to the care provider electronic device(s) 204 (or to signal an electronic device where such medical information is stored to transmit such medical information to the care provider electronic device) separate from the transmitted alerts.

In yet another example, the electronic device 101 may monitor data from sensor(s) 206 to determine whether or not a care event has occurred, but the communication component 207 may not be capable of communicating with the care provider electronic device 204 (whether because the communication component utilizes a different communication media from the care provider electronic device, the electronic device is out of range for a communication media share with the care provider electronic device, and/or any other such reason why the communication component cannot communicate with the care provider electronic device) but may be capable of communicating with the cooperative electronic device 103. In one example case, the electronic device may only include a Bluetooth low energy communication component whereas the cooperative electronic device includes a cellular antenna. As such, the electronic device may signal the cooperative electronic device to transmit the alert to the care provider electronic device.

In another example case, the electronic device 101 may be part of a mesh network. In some cases, the care provider electronic device 204 may be part of the mesh network but the electronic device may not be within range and the transmitted alert may related from the electronic device to a cooperative electronic device that is within range and subsequently relayed (whether immediately, at a delay, or when the cooperative electronic device comes within range of another cooperative electronic device) in the mesh network until the alert reaches the care provider electronic device. In other cases, the care provider electronic device 204 may not be part of the mesh network the transmitted alert may related from the electronic device to a cooperative electronic device that is part of the mesh network and subsequently relayed in the mesh network until the alert reaches a cooperative electronic device that can communicate with the care provider electronic device, which then may relay the alert accordingly.

In various implementations, the electronic device 101 may transmit alerts regarding a detected occurrence of a care event to one or more care provider electronic devices 204 associated with one or more entities included in a user defined (or otherwise defined) care list. Such a care list may include information utilized to transmit care alerts (such as contact information, communication media to utilize, and so on) and/or various conditions and/or rules under which alerts may be transmitted to various care providers.

In some cases, a care list may be defined to include multiple levels. Such multiple levels may be ranked sets of members. In some cases, care list members may be ranked in levels such that alerts regarding an occurrence are first transmitted to a first level of members and then to a second level of members if an escalation condition occurs. Such escalation conditions may include elapse of a timeout period, escalation of the detected care event occurrence, failure to receive acknowledgement from the first level of members, receipt of an indication from the first level of members to escalate (such as an indication that the first level members will be unable to respond appropriately), and/or any other such reason to escalate to a second level of members.

Figure 8:
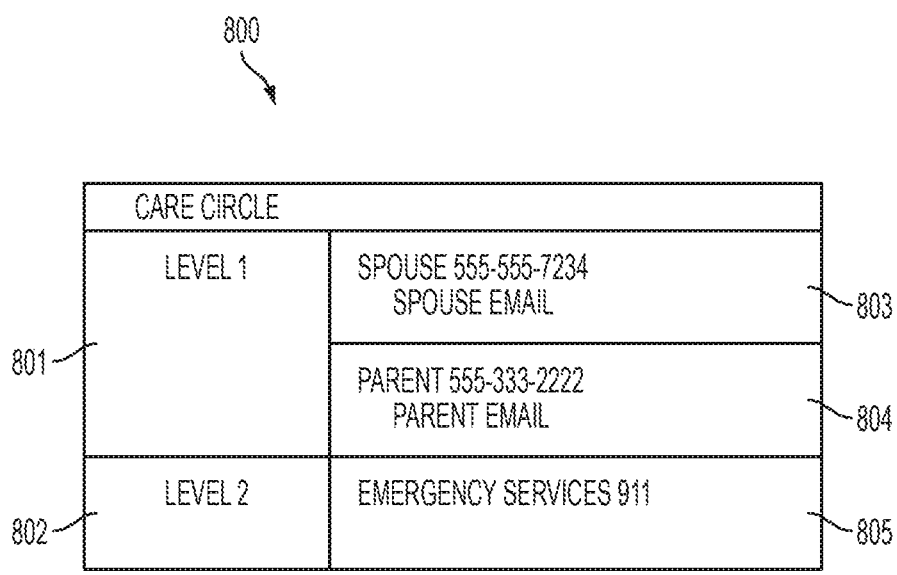
FIG. 8 is a table illustrating an example care list. Such a care list may be utilized by the example systems of FIGS. 1 and/or 2 and/or in the example methods of FIGS. 3-7.

FIG. 8 is a table 800 illustrating an example care list. As illustrated, the table includes a first level 801 including a first entry 803 for a user's spouse and a second entry 804 for the user's parent and a second level 802 including an entry 805 for emergency services. As also illustrated, the entries for the user's spouse and parent may include a telephone number to which telephone calls may be placed and/or to which text messages may be sent and email addresses to which emails may be sent. Further, the entry for emergency services may include an emergency services telephone number to which telephone calls may be placed to request emergency services.

Returning to FIG. 2, the electronic device 101 may utilize a care list configured as in the table 800 of FIG. 8. Upon detection of an occurrence, the electronic device may transmit (and/or cooperate with one or more cooperative electronic devices 103 to transmit) alerts to the telephone numbers and/or emails of the user's spouse and parent. Upon the elapse of a period of time such as a half an hour, the electronic device may determine that the user's spouse and parent have been unable to respond. As such, the electronic device may then determine the situation has escalated and transmit alerts to emergency services.

A care list may also include one or more conditions specifying different procedures to be followed in transmitting alerts based on factors such as the particular occurrence detected. For example, if an electronic device 101 utilizing a care list configured as in table 800 of FIG. 8 detects a relatively less serious care event such as an elderly user has fallen and should be checked on, the electronic device may transmit alerts according to the levels of the care list as normal. However, if the electronic device detects a relatively more serious care event such as a failure to detect a heartbeat, the electronic device may skip the first level and immediately transmit alerts to emergency services (or transmit alerts to both levels simultaneously).

A care list may also include one or more conditions related to a context of the electronic device 101. For example, if one or more entries specify communication media that the electronic device is unable to utilize (such as where the electronic device does not utilize such a media or whether the media is currently unavailable such as in the case of being out of range), one or more conditions may specify one or more other entries to utilize which specify a communication media that the electronic device is able to utilize. In some cases, an entry may specify an email address but the electronic device may not currently be in a data network. As such, the electronic device may instead utilize an entry that has a telephone number that the electronic device is capable of contacting via an available non-data cellular network.

In cases where no communication media are currently utilizable by the electronic device 101, the electronic device may utilize other means of transmitting alerts than those specified in such a care list. For example, if the electronic device (and/or one or more cooperative electronic devices 103) includes a GPS device, such a GPS device may be utilized to transmit GPS SOS alerts.

By way of another example, the care list may include a first level of entries that are telephone numbers for family and/or friends local to a user's home city and a second level including a telephone number for emergency services that functions throughout the user's country. If the electronic device 101 is located outside of the user's home city when an occurrence is detected, the electronic device may transmit alerts to emergency services instead of (or in addition to) the user's family and/or friends under the assumption that the user's family and/or friends may not be proximate enough to the user to provide care for the detected care event but that emergency services in the user's current location will be able to respond.

By way of yet another example, the care list may include a telephone number for emergency services in a user's home country. If the electronic device 101 is located outside of the user's home country when an occurrence is detected, the electronic device may obtain (and/or utilize one or more cooperative electronic devices 103 to obtain) a telephone number for local emergency services and transmit alerts to that telephone number instead.

Although the conditions above related to use of such a care list have been described as included in the care list, it is understood that these are examples. In various implementations, such conditions may be stored outside of such a care list by the electronic device 101 and/or one or more cooperative electronic devices 103 and evaluated when appropriate.

In various implementations, the electronic device 101 may include a variety of information in transmitted alerts. Such information may include the monitored environmental data, the user data, a portion thereof, information regarding the user and/or the electronic device, medical records and/or other medical data for the user, positional information, and/or any other such information that may be relevant to the care event and/or responding to the care event.

For example, the transmitted alert may include information identifying the care event for which an occurrence has been detected. In some cases, the electronic device 101 may monitor acceleration data from an accelerometer. From such data, the electronic device may determine that an acceleration corresponding to travel in an automobile was detected followed by a sudden stop. As such, the electronic device may determine that a user has been in an automobile accident and transmit one or more alerts indicating that an automobile accident has occurred. As the alert may specify this information, care providers may be able to respond appropriately to the particular care event that may have occurred.

By way of another example, the transmitted alert may include position and/or location information (such as position and/or location information from a GPS device included in the electronic device 101 and/or one or more cooperative electronic devices 103) identifying where the detected care event has occurred. Such information may enable care providers to locate the user in order to respond to the care event. Such information may also enable care providers to respond more appropriately to care events. For instance, information included in an alert identifying that a user has a heart attack in a shopping mall may enable a care provider to dispatch an ambulance whereas information included in an alert indicating that a user has fallen off of a mountain in a wilderness area may enable the care provider to dispatch a search and rescue helicopter.

By way of still another example, the transmitted alert may include medical records and/or other medical information for a user. If the electronic device detects that a user's heart has stopped, such information may be included in a transmitted alert so that care providers can ensure that responders are prepared to resuscitate the user. Further, the transmitted alert may include medical records for the user such as a specification of the user's blood type so that responders may bring appropriately typed blood if an immediate transfusion may be necessary.

In some cases, the electronic device 101 may store such medical records or other medical information and/or obtain such from one or more cooperative electronic devices 103 in order to include such in one or more transmitted alerts. However, in other cases the electronic device may signal other devices to transmit such information. For example, the electronic device may signal a computer system associated with a user's doctor to forward the user's medical information to a care provider, thus operating as an automated consent for release of medical records.

In various implementations, the electronic device 101 may present one or more prompts via one or more input/output components 208 prior to transmitting an alert in response to detection of a care event occurrence. This may reduce the possibility of false care event occurrence detection and/or enable a user to provide additional information. In such implementations, the alert may only be transmitted after such a prompt if a user does not respond within a period of time and/or if the user affirmatively responds (such as by voice, motion or gesture such as a head shake captured by camera or other device, and/or other captured input) that an alert should be transmitted.

If the user affirmatively responds to transmit an alert in response to such a prompt, the user's response may be included in the alert. For example, an electronic device 101 may detect that a user has fallen. The electronic device may provide an audio prompt asking if the user requires assistance. In response, the user may audibly state that the user believes himself to be having a heart attack. The electronic device may capture such a voice response and include the voice response in an alert transmitted to emergency personnel. In this way, emergency personnel may be better able to evaluate the user's condition prior to responding.

In some implementations, the determination of whether or not a care event has occurred may be dependent on a context such as a context of the electronic device 101. For example, an electronic device may monitor an accelerometer for acceleration data indicating that a user may have fallen from a height (such as by a sudden downward acceleration), such as off a cliff. However, in an example instance where such data is detected, the electronic device may utilize location information from a GPS device to determine that the electronic device is present as a bungee jumping facility. Based on such a determined location, the electronic device may determine that a care event has not occurred unless the acceleration data indicates that a bungee accident has occurred.

In various implementations, the electronic device 101 (and/or one or more cooperative electronic devices 103) may display medical records and/or other information and/or one or more various haptic notifications regarding such presentation in addition to and/or instead of transmitting alerts. For example, after detecting that a user may have experienced a heart attack, an electronic device 101 may display a visual indication that a user is diabetic and may periodically vibrate to indicate that such information is presented. This may enable care providers to be alerted to such information when responding and may also assist care providers in locating the user upon arrival.

By way of another example, the electronic device 101 may transmit such medical records and/or other information and/or associated haptic notifications to electronic devices within close proximity to the electronic device (such as via Bluetooth low energy, near field communication, GPS SOS alerts, and so on). As such, electronic devices of care providers arriving on scene may receive and present such medical records and/or other information and/or associated haptic notifications, alerting the care providers to the information and/or the location of the user.

In some implementations, the environmental data monitored by the electronic device 101 (and/or one or more cooperative electronic devices 103) may relate to proximity and/or connection to one or more monitored electronic devices and/or the relationship of the electronic device to one or more geographical boundaries. For example, the electronic device may periodically send query messages to a monitored electronic device and receive responses from the monitored electronic device. If responses are not received, the electronic device may transmit alerts regarding such. In some cases, the responses may include a geographical position of the monitored device. As such, the electronic device may store previous responses such that a path of the monitored device prior to losing contact can be determined and/or a future potential path of the monitored device after losing contact may be projected.

In another example, a child's phone may monitor the proximity of a parent's phone. If the child's phone is not within a threshold proximity of (or loses connection to) the parent's phone, such as twenty feet, the child's phone may determine a care event has occurred and begin transmitting one or more alerts. In some cases, such alerts may be broadcasted, functioning as an "Amber Alert" to notify electronic devices proximate to the child's phone that the child has become separated from the parent.

In yet another example, an electronic device 101 may be a monitor worn by a dementia patient that monitors the relationship of the monitor to a geographic boundary such as a hundred feet area surrounding the patient's home. If the patient goes more than a hundred feet from the patient's home, the monitor may determine a care event has been detected and begin transmitting one or more alerts.

In still another example, a group hikers may all wear electronic devices 101 that all monitor a connection to each other. If one of the devices is no longer connected to the other devices, the respective device may begin transmitting alerts indicating where the device is located and which other devices it is still and is not still connected to. In this way, care providers may know which and how many hikers may be lost. If connection is reestablished, transmission of alerts may cease and/or one or more alerts may be transmitted to indicate that a care event did not occur after all.

In various implementations, the electronic device 101 (and/or one or more cooperative electronic devices 103) may enter into one or more power saving modes when transmitting alerts, presenting information and/or haptic output, and so on after detection of a care event occurrence. Such a power saving state may mitigate the possibility that a battery or other energy storage component of the electronic device does not lose power before care can be provided and thus conserve power for alerts, notifications, and/or presentation of related information.

For example, upon detection of a care event occurrence, an electronic device 101 may cease providing power to any component not needed for transmitting alerts. In this way, the electronic device may continue transmitting alerts for a longer period of time before consuming all available power than if the other components were allowed to continue consuming power.

In some cases, an electronic device 101 may have multiple power saving modes that the electronic device may utilize upon detection of a care event occurrence. By way of example, in some cases the electronic device may cease providing power to components not necessary for transmitting alerts when a care event occurrence is first detected, preserving available power for alert transmission, and may transmit alerts every minute. However, after a period of time such as an hour, the electronic device may enter a further powered down state by only transmitting alerts every half hour. Such a procedure of multiple power saving levels may maximize the possibility of alerting care providers immediately with the possibility that care providers will be eventually alerted before available power is consumed entirely.

Figure 3:
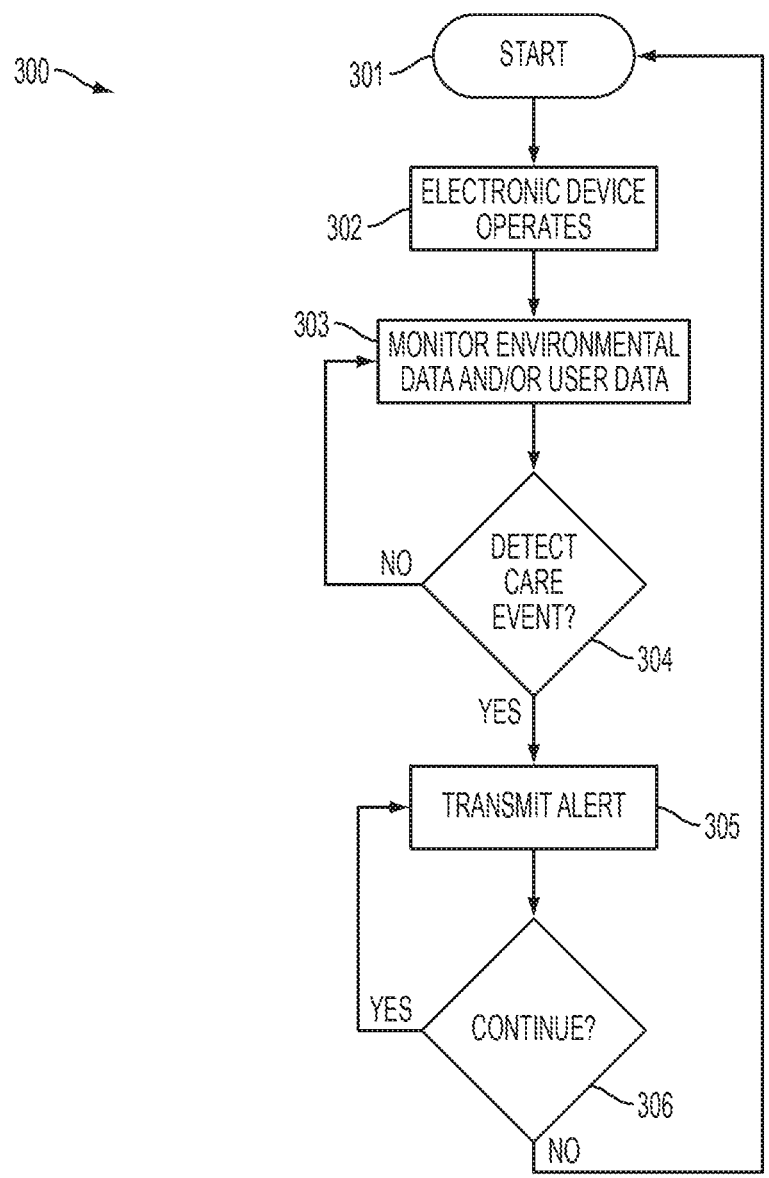
FIG. 3 is a flow chart illustrating a first example method for providing alerts regarding a care event. This method may be performed by the example systems of FIGS. 1 and/or 2.

FIG. 3 is a flow chart illustrating a first example method 300 for providing alerts regarding a care event. This method may be performed by the example systems of FIGS. 1 and/or 2.

The flow may begin at block 301 and may proceed to block 302 where an electronic device operates. The flow then may proceed to block 303 where the electronic device monitors environmental data and/or user data from one or more sensors. Next, the flow may proceed to block 304 where the electronic device determines whether or not a care event is detected based on the monitored data. If so, the flow may proceed to block 305. Otherwise, the flow may return to block 302 where the electronic device continues to operate.

At block 305, after the electronic device determines that a care event has occurred, the electronic device may transmit one or more alerts to one or more care providers.

The flow then may proceed to block 306 where the electronic device determines whether or not to continue transmitting alerts. In some cases, the electronic device may continue transmitting alerts until alerts have been transmitted to all parties on a care list. In other cases, the electronic device may continue transmitting alerts until acknowledgments have been received for transmitted alerts. In still other cases, the electronic device may periodically transmit acknowledgements, such as at one or more time intervals.

If the electronic device determines to continue transmitting alerts, the flow may return to block 305 where the electronic device transmits one or more alerts. Otherwise, the flow may return to block 302 where the electronic device continues to operate.

Although the example method 300 is illustrated and described above as including particular operations performed in a particular order, it is understood that this is an example. In various cases, various orders of the same, similar, and/or different operations may be performed without departing from the scope of the present disclosure.

For example, the example method 300 is illustrated and described above as returning to block 302 after determining to not continue transmitting alerts regarding a detected occurrence. However, in various implementations the electronic device may return to monitoring environmental and/or user data in case another care event occurs. For example, a first care event may be the detection of an irregular heartbeat for a user. Subsequently, the user's heart may stop and separate alerts regarding the stopped heartbeat may be transmitted after alerts regarding the irregular heartbeat are transmitted.

Figure 4:
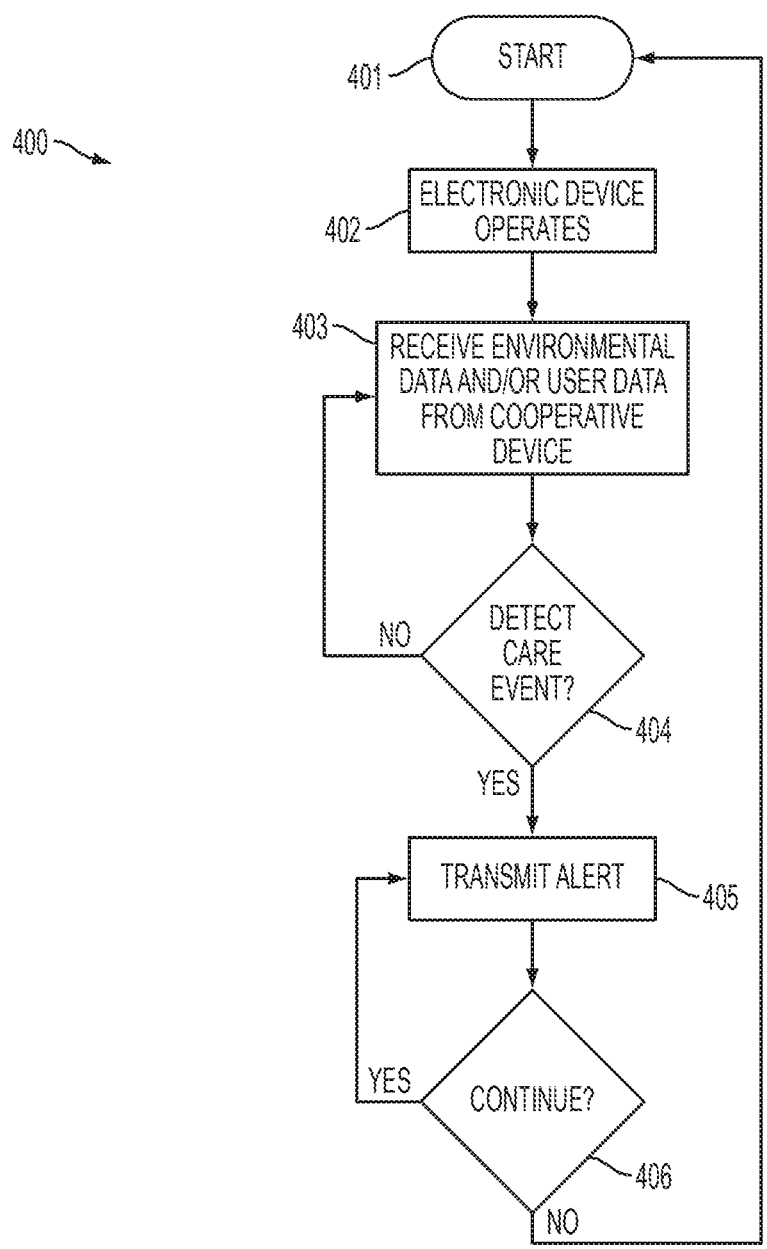
FIG. 4 is a flow chart illustrating a second example method for providing alerts regarding a care event. This method may be performed by the example systems of FIGS. 1 and/or 2.

FIG. 4 is a flow chart illustrating a second example method 400 for providing alerts regarding a care event. This method may be performed by the example systems of FIGS. 1 and/or 2.

The flow may begin at block 401 and may proceed to block 402 where an electronic device operates. The flow then may proceed to block 403 where the electronic device receives environmental data and/or user data from one or more sensors of one or more cooperative electronic devices. Next, the flow may proceed to block 404 where the electronic device determines whether or not a care event is detected based on the received data. If so, the flow may proceed to block 405. Otherwise, the flow may return to block 402 where the electronic device continues to operate.

At block 405, after the electronic device determines that a care event has occurred, the electronic device may transmit one or more alerts to one or more care providers.

The flow then may proceed to block 406 where the electronic device determines whether or not to continue transmitting alerts. If the electronic device determines to continue transmitting alerts, the flow may return to block 405 where the electronic device transmits one or more alerts. Otherwise, the flow may return to block 402 where the electronic device continues to operate.

Although the example method 400 is illustrated and described above as including particular operations performed in a particular order, it is understood that this is an example. In various cases, various orders of the same, similar, and/or different operations may be performed without departing from the scope of the present disclosure.

For example, the example method 400 is illustrated and described above as receiving the environmental and/or user data from one or more cooperative electronic devices. However, in various implementations such received data may be monitored along with data from one or more sensors of the electronic device to determine the occurrence of a care event without departing from the scope of the present disclosure.

Figure 5:
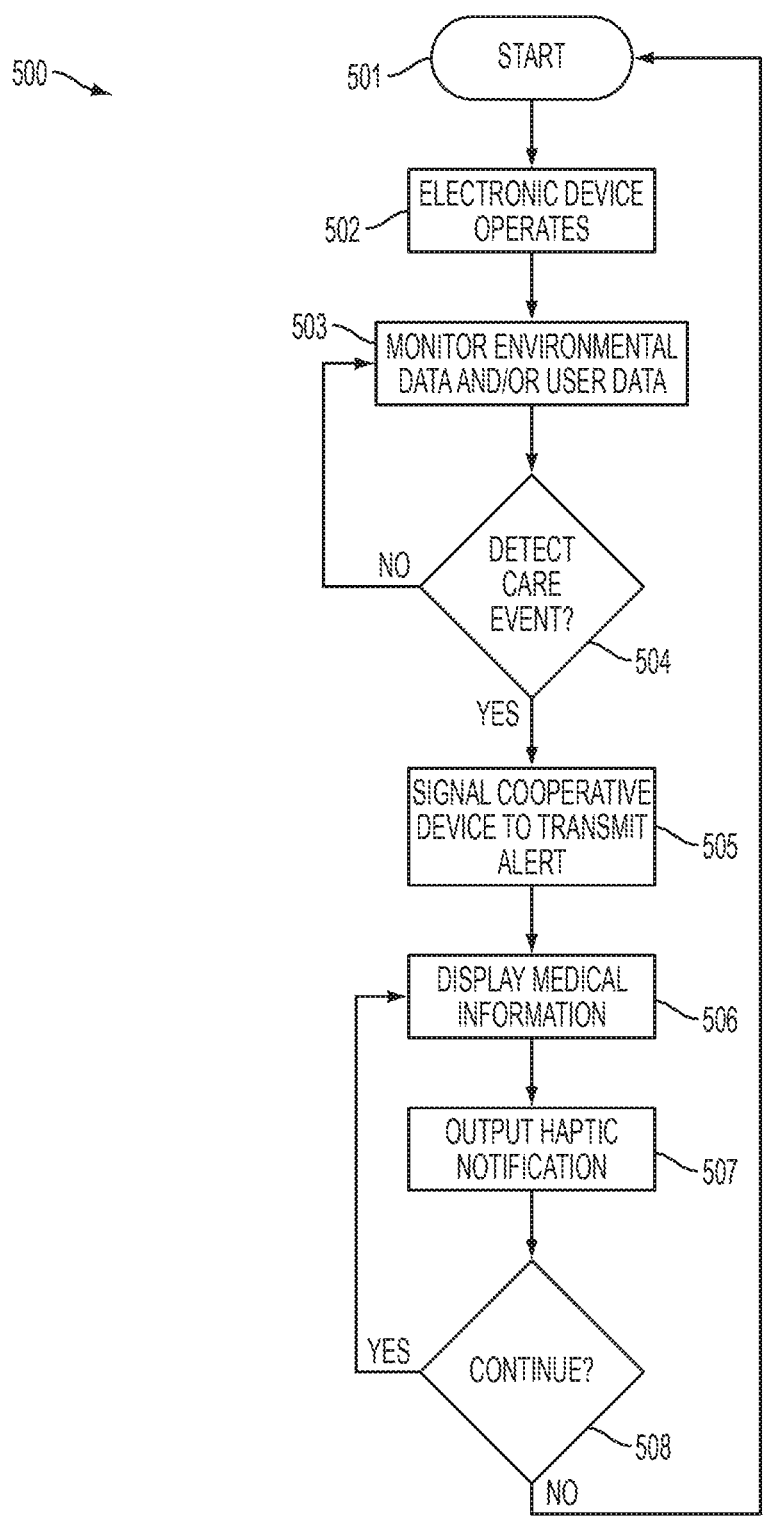
FIG. 5 is a flow chart illustrating a third example method for providing alerts regarding a care event. This method may be performed by the example systems of FIGS. 1 and/or 2.

FIG. 5 is a flow chart illustrating a third example method 500 for providing alerts regarding a care event. This method may be performed by the example systems of FIGS. 1 and/or 2.

The flow may begin at block 501 and proceeds to block 502 where an electronic device operates. The flow then may proceed to block 503 where the electronic device monitors environmental data and/or user data from one or more sensors. Next, the flow may proceed to block 504 where the electronic device determines whether or not a care event is detected based on the monitored data. If so, the flow may proceed to block 505. Otherwise, the flow may return to block 502 where the electronic device continues to operate.

At block 505, after the electronic device determines that a care event has occurred, the electronic device may signal one or more cooperative electronic devices to transmit one or more alerts to one or more care providers.

The flow then may proceed to block 506 where the electronic device presents medical information (such as on one or more displays, via one or more speakers, and so on) (such as medical records, allergies such as medicine allergies, medical conditions, medical information related to the detected occurrence, and so on). Next, the flow may proceed to block 507 one or more haptic notifications (such as one or more vibrations, audio alerts, and so on) are provided to indicate that the medical information is presented. In this way, a care provider coming upon a user of the electronic device may be alerted that medical information for the user, who may be incapacitated, is available.

The flow then may proceed to block 508 where the electronic device determines whether or not to continue present the medical information and/or outputting the haptic notifications. In some cases, the electronic device may periodically present the medical information and/or outputting the haptic notifications, such as at one or more time intervals. If so, the flow may return to block 506 where the electronic device continues presenting the medical information. Otherwise, the flow may return to block 502 where the electronic device continues to operate.

Although the example method 500 is illustrated and described above as including particular operations performed in a particular order, it is understood that this is an example. In various cases, various orders of the same, similar, and/or different operations may be performed without departing from the scope of the present disclosure.

For example, the example method 500 is illustrated and described above as presenting the medical information itself. However, in various implementations the electronic device may signal other electronic devices to present the medical information. For example, the electronic device may broadcast such information via a communication medium such as Bluetooth low energy such that an electronic device of a care provider coming upon a user of the electronic device may present such medical information and/or one or more haptic notifications regarding the presentation of such medical information.

Figure 6:
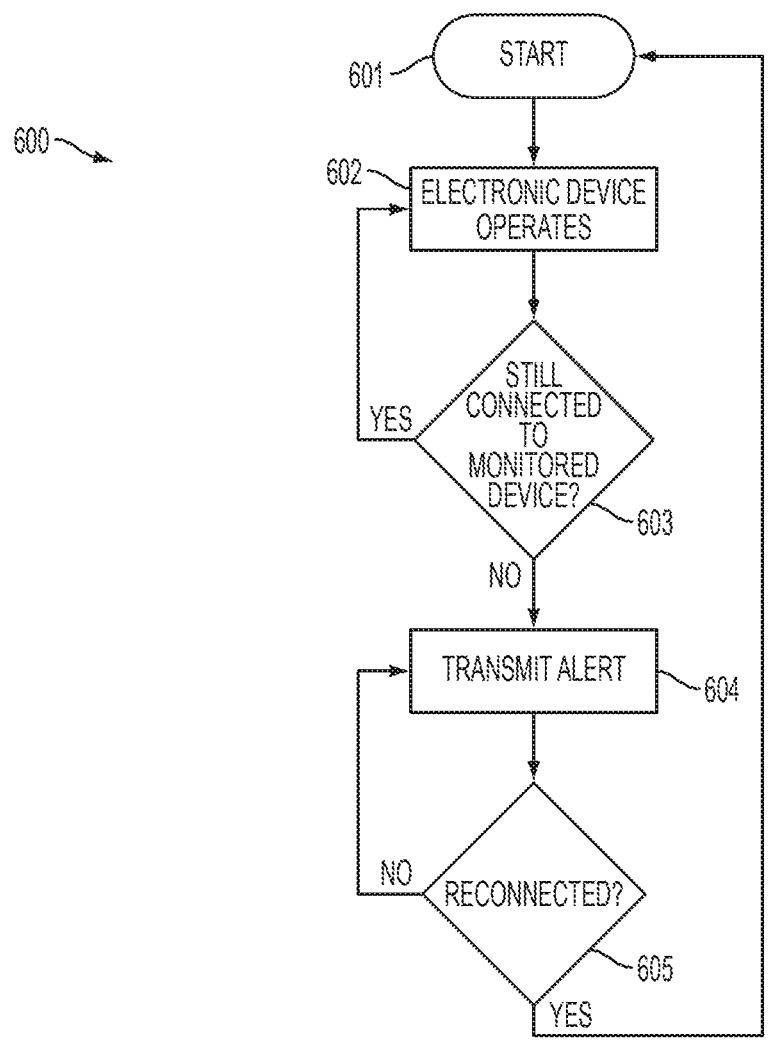
FIG. 6 is a flow chart illustrating a fourth example method for providing alerts regarding a care event. This method may be performed by the example systems of FIGS. 1 and/or 2.

FIG. 6 is a flow chart illustrating a fourth example method for providing alerts regarding a care event. This method may be performed by the example systems of FIGS. 1 and/or 2.

The flow may begin at block 601 and may proceed to block 602 where the electronic operates. The flow then may proceed to block 603 where the electronic device determines whether or not the electronic device is still connected to a monitored device. Connection between the electronic device and the monitored device may be determined based on whether or not expected signals are received from the monitored device, comparison of a distance between the two devices to a threshold (wherein they are determined connected if within the threshold and determined no longer connected if they are not within the threshold), and/or any other such determination of connection.

If the electronic device is not still connected to the monitored device, the flow proceeds to block 604. Otherwise, the flow returns to block 602 where the electronic device continues to operate.

At block 604, the electronic device may transmit one or more alerts to one or more care providers. The flow may then proceed to block 605 where the electronic device may determine whether or not the electronic device is reconnected to the monitored device. If so, the flow may return to block 602 where the electronic device continues to operate. If not, the flow may return to block 605 where the electronic device may continue transmitting alerts.

Although the example method 600 is illustrated and described above as including particular operations performed in a particular order, it is understood that this is an example. In various cases, various orders of the same, similar, and/or different operations may be performed without departing from the scope of the present disclosure.

For example, the example method 600 is illustrated and described above as determining whether or not the electronic device is still connected to a monitored device at block 603. However, in other implementations the electronic device may instead determine whether or not the electronic device is within a geographical boundary instead of determining without departing from the scope of the present disclosure.

Figure 7:
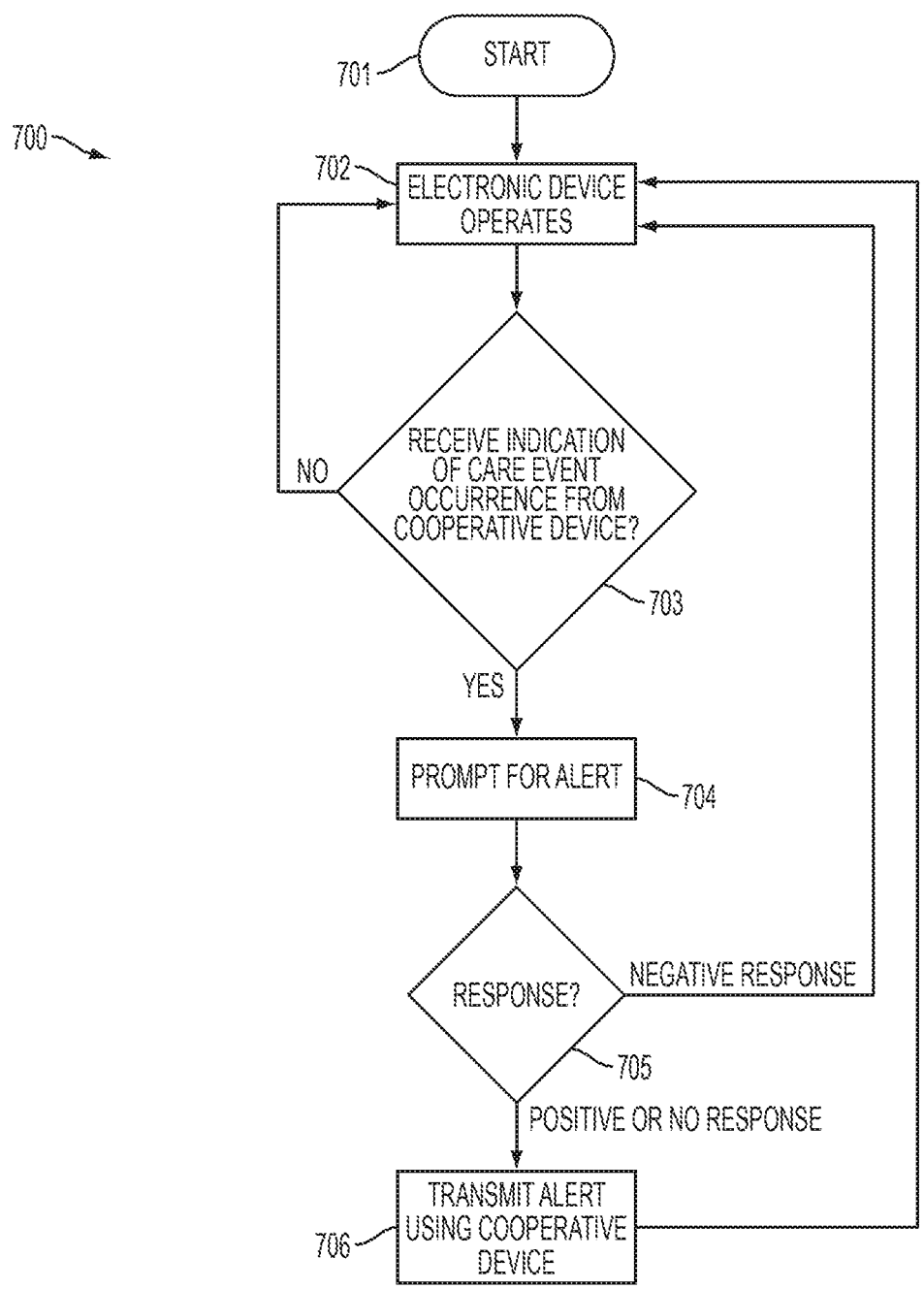
FIG. 7 is a flow chart illustrating a fifth example method for providing alerts regarding a care event. This method may be performed by the example systems of FIGS. 1 and/or 2.

FIG. 7 is a flow chart illustrating a fifth example method for providing alerts regarding a care event. This method may be performed by the example systems of FIGS. 1 and/or 2.

The flow may begin at block 701 and may proceed to block 702 where an electronic device operates. The flow then may proceed to block 703 where the electronic device determines whether or not an indication from a cooperative electronic device that a care event has been detected is received. If so, the flow may proceed to block 704. Otherwise, the flow may return to block 702 where the electronic device continues to operate.

At block 704, after the electronic device determines that an indication from a cooperative electronic device that a care event has been detected is received, the electronic device may present one or more prompts regarding whether or not an alert should be transmitted. The flow may then proceed to block 705 where the electronic device may determine whether a negative response, a positive response, or no response, has been received within a timeout period.

If a negative response is received, the flow may return to block 702 and the electronic device may continue to operate. Otherwise, the flow may proceed to block 706 where the electronic device may signal the cooperative electronic device to transmit one or more alerts.

Although the example method 700 is illustrated and described above as including particular operations performed in a particular order, it is understood that this is an example. In various cases, various orders of the same, similar, and/or different operations may be performed without departing from the scope of the present disclosure.

For example, the example method 700 is illustrated and described above as signaling the same cooperative electronic device to transmit alerts from which the indication regarding a detected care event was received. However, in various implementations these functions may be performed by one or more different cooperative electronic devices.

As described above and illustrated in the accompanying figures, the present disclosure discloses systems, methods, and apparatuses for providing alerts regarding a care event. An occurrence of one or more care events is detected by an electronic device monitoring environmental data and/or user data from one or more sensors. The electronic device transmits one or more alerts regarding the detected occurrence to at least one other electronic device. In some cases, the electronic device may cooperate with at least one other electronic device (a cooperative electronic device) in monitoring, detecting, and/or transmitting. For example, the electronic device may detect the occurrence based on sensor data received from a cooperative electronic device or such data in combination with the electronic device's sensor data. By way of another example, the electronic device may detect the occurrence and signal a cooperative electronic device to transmit one or more alerts.

In the present disclosure, the methods disclosed may be implemented as sets of instructions or software readable by a device. Further, it is understood that the specific order or hierarchy of steps in the methods disclosed are examples of sample approaches. In other embodiments, the specific order or hierarchy of steps in the method can be rearranged while remaining within the disclosed subject matter. The accompanying method claims present elements of the various steps in a sample order, and are not necessarily meant to be limited to the specific order or hierarchy presented.

The described disclosure may be provided as a computer program product, or software, that may include a non-transitory machine-readable medium having stored thereon instructions, which may be used to program a computer system (or other electronic devices) to perform a process according to the present disclosure. A non-transitory machine-readable medium includes any mechanism for storing information in a form (e.g., software, processing application) readable by a machine (e.g., a computer). The non-transitory machine-readable medium may take the form of, but is not limited to, a magnetic storage medium (e.g., floppy diskette, video cassette, and so on); optical storage medium (e.g., CD-ROM); magneto-optical storage medium; read only memory (ROM); random access memory (RAM); erasable programmable memory (e.g., EPROM and EEPROM); flash memory; and so on.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes.

While the present disclosure has been described with reference to various embodiments, it will be understood that these embodiments are illustrative and that the scope of the disclosure is not limited to them. Many variations, modifications, additions, and improvements are possible. More generally, embodiments in accordance with the present disclosure have been described in the context or particular embodiments. Functionality may be separated or combined in blocks differently in various embodiments of the disclosure or described with different terminology. These and other variations, modifications, additions, and improvements may fall within the scope of the disclosure as defined in the claims that follow.

We claim:

1. An electronic device, comprising:
a sensor that gathers sensor data;
processing circuitry configured to:
monitor the sensor data to detect that a user has fallen;
present a prompt in response to detecting that the user has fallen;
monitor the sensor data to detect a motion response by the user within a time period after the prompt is presented; and
detect a positive response to the prompt within the time period; and
communication circuitry that transmits an alert after an additional time period if the motion response is not detected, wherein the communication circuitry transmits the alert before the additional time period if the positive response is detected.

2. The electronic device defined in claim 1, further comprising a touch screen, wherein the positive response comprises a touch input on the touch screen.

3. The electronic device defined in claim 1, wherein the prompt comprises an audio notification.

4. The electronic device defined in claim 3, wherein the prompt further comprises a haptic notification.

5. The electronic device defined in claim 1, wherein the alert includes location data.

6. The electronic device defined in claim 1, further comprising a heart rate sensor.

7. The electronic device defined in claim 6, wherein the processing circuitry monitors heart rate data collected by the heart rate sensor to detect an irregular heart rate of the user and presents an additional prompt in response to detecting the irregular heart rate.

8. A wearable electronic device having first and second opposing sides, the wearable electronic device comprising:
- a display on the first side, wherein the second side is configured to face a user's arm;
- a sensor that collects sensor data;
- processing circuitry that monitors the sensor data to detect a fall by the user and to detect a motion by the user after the fall, wherein the processing circuitry displays a prompt in response to detecting the fall, and wherein the processing circuitry monitors the sensor data to detect a negative response to the prompt from the user; and
- wireless communication circuitry that transmits an alert if the motion is not detected unless the negative response to the prompt is detected.

9. The wearable electronic device defined in claim 8, wherein the negative response comprises a touch input.

10. The wearable electronic device defined in claim 9, wherein the alert is transmitted to emergency services automatically without user input.

11. The wearable electronic device defined in claim 10, wherein the alert is transmitted to local emergency services based on a location of the wearable electronic device.

12. The wearable electronic device defined in claim 10, wherein the alert includes a location of the wearable electronic device.

13. The wearable electronic device defined in claim 12, wherein the alert includes a voice response from the user.

14. The wearable electronic device defined in claim 8, wherein the display forms a majority of the first side.

15. The wearable electronic device defined in claim 8, wherein the display displays information regarding the fall.

16. The wearable electronic device defined in claim 8, wherein the wearable electronic device enters into a power saving mode in response to detecting the fall.

17. The electronic device defined in claim 1, wherein the alert comprises an audio alert and GPS information and wherein the alert is transmitted to emergency services.

18. An electronic device, comprising:
- a sensor that gathers sensor data;
- processing circuitry configured to:
  - monitor the sensor data to detect that a user has fallen;
  - present a prompt in response to detecting that the user has fallen;
  - monitor the sensor data to detect a motion by the user within a time period; and
  - detect a positive response to the prompt within the time period; and
- communication circuitry that transmits an alert after an additional time period if the motion is not detected, wherein the communication circuitry transmits the alert before the additional time period if the positive response is detected.

* * * * *